(12) United States Patent
Kunieda et al.

(10) Patent No.: US 8,207,131 B2
(45) Date of Patent: Jun. 26, 2012

(54) PEPTIDE

(75) Inventors: Yukiko Kunieda, Tokyo (JP); Satoshi Higurashi, Saitama (JP); Mutsumi Motouri, Saitama (JP); Hiroaki Matsuyama, Saitama (JP); Atsushi Serizawa, Saitama (JP); Hiroshi Kawakami, Saitama (JP)

(73) Assignee: Megmilk Snow Brand Co., Ltd., Sapporo (JP)

( * ) Notice: Subject to any disclaimer, the term of this patent is extended or adjusted under 35 U.S.C. 154(b) by 519 days.

(21) Appl. No.: 12/298,190

(22) PCT Filed: Apr. 25, 2007

(86) PCT No.: PCT/JP2007/058926
§ 371 (c)(1),
(2), (4) Date: Mar. 4, 2009

(87) PCT Pub. No.: WO2007/125946
PCT Pub. Date: Nov. 8, 2007

(65) Prior Publication Data
US 2010/0075909 A1 Mar. 25, 2010

(30) Foreign Application Priority Data

Apr. 28, 2006 (JP) .................................. 2006-125283
Apr. 28, 2006 (JP) .................................. 2006-126103

(51) Int. Cl.
*A61K 38/08* (2006.01)
*A61K 38/06* (2006.01)
*A61K 38/07* (2006.01)
*A61K 38/04* (2006.01)
*C07K 5/00* (2006.01)
*C07K 7/00* (2006.01)
*C07K 16/00* (2006.01)
*C07K 17/00* (2006.01)

(52) U.S. Cl. ..................... 514/21.6; 514/21.8; 514/21.9; 530/328; 530/329; 530/330

(58) Field of Classification Search ........................ None
See application file for complete search history.

(56) References Cited

U.S. PATENT DOCUMENTS 6,426,102 B1 * 7/2002 Isom et al. ..................... 426/72
2005/0281914 A1 12/2005 Broadbent et al.
2007/0203060 A1 * 8/2007 Sidelman ........................ 514/12

FOREIGN PATENT DOCUMENTS

| JP | 2005-60308 | 3/2005 |
| WO | WO 2005/081628 | 9/2005 |
| WO | WO 2006/068480 | 6/2006 |

OTHER PUBLICATIONS

Satoshi Higure et al., "Cheese no Naizo Shibo Chikuski Yokusei Sayo oyobi Adiponectin Teika Yokuseki Sayo", The Japanese Society of Nutrition and Food science Taikai Koen Yoshishu, vol. 60$^{th}$, p. 353, Apr. 1, 2006.
Yukiko Kunieda et al., "Gouda Cheese Yurai Kosanka Peptide no Bunri to Dotel", Japan Society for Bioscience, Bioscience, Biotechnology, and Agrochemistry 2006 Nendo (Heisei 18 Nendo) Taikai Koen Yoshishu, Mar. 5, 2006, p. 69, 2J15p20.
Gao Tang et al.—Research on Gouda cheese Holland—1. Agriculture Department of Yangling Vocational & Technical College, Yangling, 712100; 2. Northwest Sci—Tech University of Agriculture & Forestry, Yangling, 712100—No. 3. 2003—pp. 10-12.
Koji Nagao et al.—Biochemical and Molecular Actions of Nutrients—Dietary Conjugated Linoleic Acid Alleviates Nonalcoholic Fatty Liver Disease in Zucker (fa/fa) Rats—Oct. 4, 2004—pp. 5-9.
Chinese Official Action—200780015488.3—May 25, 2011.

* cited by examiner

*Primary Examiner* — Marcela M Cordero Garcia
(74) *Attorney, Agent, or Firm* — Young & Thompson

(57) ABSTRACT

The present invention relates to a peptide that is derived from a milk protein and has an antioxidative effect, an antioxidant that includes the peptide as an active ingredient, and an antioxidative food, drink, or feed that includes the peptide. The present invention also relates to a peptide that is derived from a milk protein and has an adiponectin production promotion effect, an adiponectin production promoter that includes the peptide as an active ingredient, and an adiponectin production promotion food, drink, or feed that includes the peptide. The present invention further relates to a blood adiponectin level increase promotion and/or decrease inhibition agent that includes a component contained in cheese as an active ingredient, and a blood adiponectin level increase promotion and/or decrease inhibition food or drink that includes a component contained in cheese. The present invention to the peptide that consists of an amino acid sequence shown by His-Pro-Ile-Lys-His-Gln-Gly-Leu-Pro-Gln (1), His-Pro-Ile-Lys (2) or His-Gln-Gly-Leu-Pro-Gln (3), and has an antioxidative effect.

6 Claims, 5 Drawing Sheets

PEPTIDE

TECHNICAL FIELD

The present invention relates to a peptide that is derived from a milk protein and has an antioxidative effect, an antioxidant that includes the peptide as an active ingredient, and an antioxidative food, drink, or feed that includes the peptide.

The present invention also relates to a peptide that is derived from a milk protein and has an adiponectin production promotion effect, an adiponectin production promoter that includes the peptide as an active ingredient, and an adiponectin production promotion food, drink, or feed that includes the peptide.

The present invention further relates to a blood adiponectin level increase promotion and/or decrease inhibition agent that includes a component contained in cheese as an active ingredient, and a blood adiponectin level increase promotion and/or decrease inhibition food or drink that includes a component contained in cheese.

BACKGROUND ART

Peroxides and free radicals produced by oxidation of unsaturated fatty acids impair the flavor and the nutritive value of food so that a deterioration in quality occurs, for example. Moreover, such peroxides and free radicals cause damage to proteins and DNA in cells due to strong oxidizing power, and cause damage to lipids that form cell membranes to produce highly toxic lipid peroxides (e.g., hydroperoxides) so that cellular damage or tissue damage occurs. It has been revealed that accumulation of adverse effects of active oxygen and free radicals on the living body promotes aging and causes lifestyle-related diseases including cancer, arteriosclerosis, and heart disease. In particular, since lifestyle-related disease is closely related to diet, the importance of improvement in diet on disease prevention has attracted attention. Therefore, research on the relationship between the antioxidative properties of food and food ingredients and research on antioxidative ingredients have been conducted from the viewpoint of preventing or suppressing oxidative stress due to food ingredients.

Plant-derived vitamins, polyphenols, and the like have been known as antioxidative ingredients. Various reports on antioxidative vitamins have been made. In particular, it has been confirmed that vitamin C, vitamin E, β-carotene, and the like have antioxidative properties. Regarding polyphenols, it has been revealed that catechins, flavonoids, and the like have strong antioxidative properties. Various antioxidative peptides have been isolated and identified from protease hydrolyzates of proteins. Three antioxidative peptides have been isolated from an enzymatic decomposition product of egg albumin (see Non-patent Document 1, for example). Six antioxidative peptides have been isolated and identified from a protease hydrolyzate of β-conglycinin (soybean protein) (see Non-patent Document 2, for example).

Enzymatic decomposition products of milk proteins have physiological activities such as an opioid activation effect, a calcium resorption promotion effect, a cell growth effect, an antibacterial effect, and an angiotensin I-converting enzyme inhibitory effect. A method that emulsifies eicosapentaenoic acid-containing oils and fats such as fish oil using a water-soluble protein solution to suppress fish oil odor (see Patent Document 1, for example), and a method that emulsifies highly unsaturated fatty acid-containing oils and fats using a partial hydrolyzate of milk to obtain a powder of the highly unsaturated fatty acid-containing oils and fats with high oxidation stability (see Patent Document 2, for example) have been disclosed. A method that emulsifies highly unsaturated fatty acid-containing oils and fats, cheese, and water to prepare an antioxidative emulsified product to prevent oxidation of the highly unsaturated fatty acid-containing oils and fats and prevent fish odor from highly unsaturated fatty acid-containing fish oils and fats and a foul smell during storage has also been disclosed (see Patent Document 3, for example). The emulsified products of highly unsaturated fatty acid-containing oils and fats disclosed in the above documents are prepared by adding a water-soluble protein solution, a partial hydrolyzate of milk, or cheese to highly unsaturated fatty acid-containing oils and fats, and emulsifying the mixture. The above-mentioned methods prevent fish odor from the highly unsaturated fatty acid-containing fish oils and fats and a foul smell during storage. However, only a few reports have been made that a milk protein-derived peptide has antioxidative properties without mixing a peptide with highly unsaturated fatty acid-containing oils and fats and emulsifying the mixture. The inventors of the present invention have found that a water-soluble peptide fraction of cheese has antioxidative properties, and applied for a patent (see Patent Document 4). The inventors have also found that a peptide having a specific amino acid sequence has antioxidative properties (see Patent Document 5). However, these peptides are mainly contained in mold-ripened cheese. The worldwide production and consumption of lactic acid bacteria-ripened cheese are significantly higher than those of mold-ripened cheese. Lactic acid bacteria-ripened cheese is also utilized as a raw material for processed cheese. Therefore, it is desirable to isolate a peptide component having high antioxidative properties from lactic acid bacteria-ripened cheese.

As described above, accumulation of adverse effects of active oxygen and free radicals on the living body causes lifestyle-related diseases. It is important to prevent risk factors (e.g., hypertension, hyperlipemia, and diabetes) relating to the onset and progression of lifestyle-related disease. In Japan, the number of deaths caused by cardiovascular disease and cerebrovascular disease has increased year by year. Cardiovascular disease and cerebrovascular disease are responsible for about one-third of all deaths. Therefore, measures against cardiovascular disease and cerebrovascular disease have become important issues. The risk of these arteriosclerotic diseases increases significantly due to a combination of risk factors such as hypertension, hyperlipemia, and glucose intolerance. A combination of such risk factors is referred to as metabolic syndrome that has been widely recognized.

It is considered that prevention of excessive visceral fat accumulation is important in order to prevent metabolic syndrome. A fat tissue (i.e., a secretory tissue predominant in a living body) produces various endocrine factors, and is involved in the maintenance of homeostasis of a living body. However, excessive visceral fat accumulation breaks down the secretion balance between the endocrine factors and causes various pathological conditions. A fat tissue has been merely considered to be an energy storage. In recent years, the importance of a fat tissue has attracted attention when considering metabolic disorder syndrome including lifestyle-related disease. Specifically, a fat tissue produces endocrine factors such as a plasminogen activator inhibitor, a tumor necrosis factor (TNF-α), leptin, and adiponectin, and contributes to the maintenance of homeostasis of a living body. It has been revealed that imbalance between the endocrine factors (e.g., excessive production or underproduction) is closely related to the onset and progression of sugar/lipid metabolism disorder, hypertension, and arteriosclerosis.

Adiponectin that is an endocrine factor produced by a fat tissue is a 30 kDa hormone formed of 244 amino acids. It is considered that adiponectin has an effect of suppressing arteriosclerosis and an effect of promoting fat burning in the liver and muscle. Adiponectin has an effect of promoting incorporation of glucose and fatty acid in blood into cells. When fat is accumulated in the muscle, liver, and the like, incorporation of sugar deteriorates so that diabetes may occur. It is considered that adiponectin decomposes fat and sugar that are temporarily accumulated excessively to keep the nutrient balance in the body. The function of adipocytes that secrete adiponectin weakens with the progression of obesity so that the nutrient balance in the body is lost.

Adiponectin specifically secreted by a fat tissue is normally contained in blood at a high level. The adiponectin level decreases due to visceral fat accumulation. Adiponectin has various physiological functions such as preventing diabetes, arteriosclerosis, inflammation, and hypertension. It is very important to promote an increase in blood adiponectin level or suppress a decrease in blood adiponectin level in order to treat metabolic syndrome.

Drug therapy has been employed as measures to treat each pathological condition involved in metabolic syndrome. However, drug therapy requires a prescription and causes side effects. Even if one pathological condition is treated, a serious pathological condition may occur due to other pathological conditions. Therefore, it is necessary to regulate the balance between the endocrine factors produced by a fat tissue. A change in lifestyle is considered to be important (i.e., exercise therapy or diet therapy rather than drug therapy) in order to prevent or treat metabolic syndrome caused by visceral fat accumulation. Therefore, a food or drink that is effective for treating metabolic syndrome caused by visceral fat accumulation and can be taken safely and daily over a long time has been desired.

In recent years, research on food ingredients having a function of suppressing the progression of disease as much as possible through diet has attracted attention rather than treatment using a synthetic medicine.

Adiponectin is known to have a liver fibrosis inhibition effect, a normal hepatocyte growth promotion effect, and an anti-inflammatory effect (see Patent Document 6, for example). As an adiponectin production promoter, a composition that contains a fermented tea extract as an active ingredient (see Patent Document 7, for example), and a blood fat tissue-specific secretion protein enhancement composition that contains an extract of a deciduous sub-canopy tree (*Phyllanthus embilica*) that belongs to *Phyllanthus urinaria* (see Patent Document 8, for example) have been disclosed.

On the other hand, cheese is a high-fat-containing food, but has a blood triglyceride level decrease promotion effect and a cholesterol metabolism improvement effect (see Patent Documents 9 and 10). However, no document teaches or suggests that cheese promotes an increase in blood adiponectin level or suppresses a decrease in blood adiponectin level.
Patent Document 1: JP-A-60-102168
Patent Document 2: JP-A-2-305898
Patent Document 3: JP-A-7-274823
Patent Document 4: JP-A-2004-352958
Patent Document 5: JP-A-2005-294358
Patent Document 6: JP-A-2000-256208
Patent Document 7: JP-A-2002-363094
Patent Document 8: JP-A-2006-56836
Patent Document 9: JP-A-2003-300890
Patent Document 10: JP-A-2003-144090
Non-patent Document 1: Tsuge, N et al., Nippon Nogeikagaku Kaishi, 65, p. 1635, 1991
Non-patent Document 2: Chen, H. M. et al., J. Agric. Food Chem., 43, p. 574, 1995

DISCLOSURE OF THE INVENTION

Problem to be Solved by the Invention

An object of the present invention is to provide a peptide that has an antioxidative effect effective for suppressing oxidative disorder of a living body due to active oxygen, free radicals, and the like that impair the flavor and the nutritive value of food to cause a deterioration in quality, and adversely affect disease, aging, and the like in vivo. Another object of the present invention is to provide a peptide that promotes production of adiponectin in vivo to suppress arteriosclerosis and promote fat burning in the liver and muscle.

A further object of the present invention is to provide a blood adiponectin level increase acceleration and/or decrease inhibition agent and a blood adiponectin level increase acceleration and/or decrease inhibition food or drink that are effective for accelerating an increase in blood adiponectin level or suppressing a decrease in blood adiponectin level upon ingestion, and include a component contained in cheese that can be taken daily as an active ingredient.

Means for Solving the Problems

The inventors conducted extensive studies in order to achieve the above objects. As a result, the inventors found that a peptide consisting of an amino acid sequence shown by the following formula (1), (2), or (3) has an antioxidative effect at a low dosage. This finding has led to the completion of the present invention.

```
His-Pro-Ile-Lys-His-Gln-Gly-Leu-Pro-Gln    (1)
(SEQ ID NO: 1)

His-Pro-Ile-Lys                             (2)
(SEQ ID NO: 2)

His-Gln-Gly-Leu-Pro-Gln                     (3)
(SEQ ID NO: 3)
```

Specifically, the present invention relates to a peptide that consists of an amino acid sequence shown by the formula (1), (2), or (3) and has an antioxidative effect.

The present invention also relates to a peptide that consists of an amino acid sequence shown by the formula (1), (2), or (3) and has an antioxidative effect, the peptide being derived from a milk protein.

The present invention also relates to an antioxidant comprising at least one peptide shown by the formula (1), (2), or (3) as an active ingredient.

The present invention also relates to an antioxidative food, drink, or feed comprising at least one peptide shown by the formula (1), (2), or (3).

The inventors found that a peptide consisting of an amino acid sequence shown by the formula (1) has an effect of promoting production of adiponectin at a low dosage. This finding has led to the completion of the present invention.

Specifically, the present invention relates to a peptide that consists of an amino acid sequence shown by the formula (1) and has an adiponectin production promotion effect.

The present invention also relates to a peptide that consists of an amino acid sequence shown by the formula (1) that is derived from a milk protein and has an adiponectin production promotion effect.

The present invention also relates to an adiponectin production promoter comprising a peptide shown by the formula (1) as an active ingredient.

The present invention also relates to an adiponectin production promotion food, drink, or feed comprising a peptide shown by the formula (1).

The inventors focused on the components contained in cheese in order to prevent or improve various functional disorders of a living body using a food material that can taken daily, and checked the physiological functions of the components. As a result, the inventors found that some components have an effect of promoting an increase in blood adiponectin level or suppressing a decrease in blood adiponectin level.

The inventors found that it is possible to promote an increase in blood adiponectin level or suppress a decrease in blood adiponectin level by providing a blood adiponectin level increase acceleration and/or decrease inhibition agent or a blood adiponectin level increase acceleration and/or decrease inhibition food or drink utilizing such physiological functions. This finding has led to the completion of the present invention.

Specifically, the inventors achieved the above object by providing a blood adiponectin level increase acceleration and/or decrease inhibition agent that includes a component contained in cheese as an active ingredient, or a blood adiponectin level increase acceleration and/or decrease inhibition food or drink that includes a component contained in cheese utilizing the effect of promoting an increase in blood adiponectin level or suppressing a decrease in blood adiponectin level possessed by the component contained in cheese. The inventors conducted extensive studies on a component contained in cheese that is effective for promoting an increase in blood adiponectin level and/or suppressing a decrease in blood adiponectin level. As a result, the inventors found that a peptide contained in cheese can be used as such an active ingredient.

Effect of the Invention

The peptide according to the present invention that consists of an amino acid sequence shown by the formula (1), (2), or (3) and has an antioxidative effect is effective for suppressing oxidative disorder of a living body due to active oxygen, free radicals, and the like that impair the flavor and the nutritive value of food to cause a deterioration in quality, and adversely affect disease, aging, and the like in vivo. The peptide according to the present invention is useful as an antioxidant that includes the peptide as an active ingredient and an antioxidative food, drink, or feed that includes the peptide.

The peptide according to the present invention that consists of an amino acid sequence shown by the formula (1) and has an adiponectin production promotion effect is effective for promoting production of adiponectin, and is useful as an adiponectin production promoter that includes the peptide as an active ingredient and an adiponectin production promotion food, drink, or feed that includes the peptide.

Since the blood adiponectin level increase acceleration and/or decrease inhibition agent or the blood adiponectin level increase acceleration and/or decrease inhibition food, drink, or feed according to the present invention that includes a component contained in cheese as an active ingredient promotes an increase in blood adiponectin level and/or suppresses a decrease in blood adiponectin level upon ingestion, the blood adiponectin level increase acceleration and/or decrease inhibition agent or the blood adiponectin level increase acceleration and/or decrease inhibition food, drink, or feed according to the present invention suppresses excessive visceral fat accumulation and is effective for treating or preventing metabolic syndrome such as thrombosis, insulin resistance, sugar metabolic disorder, and hypertension.

EXPLANATION OF SYMBOLS

Figure 1:
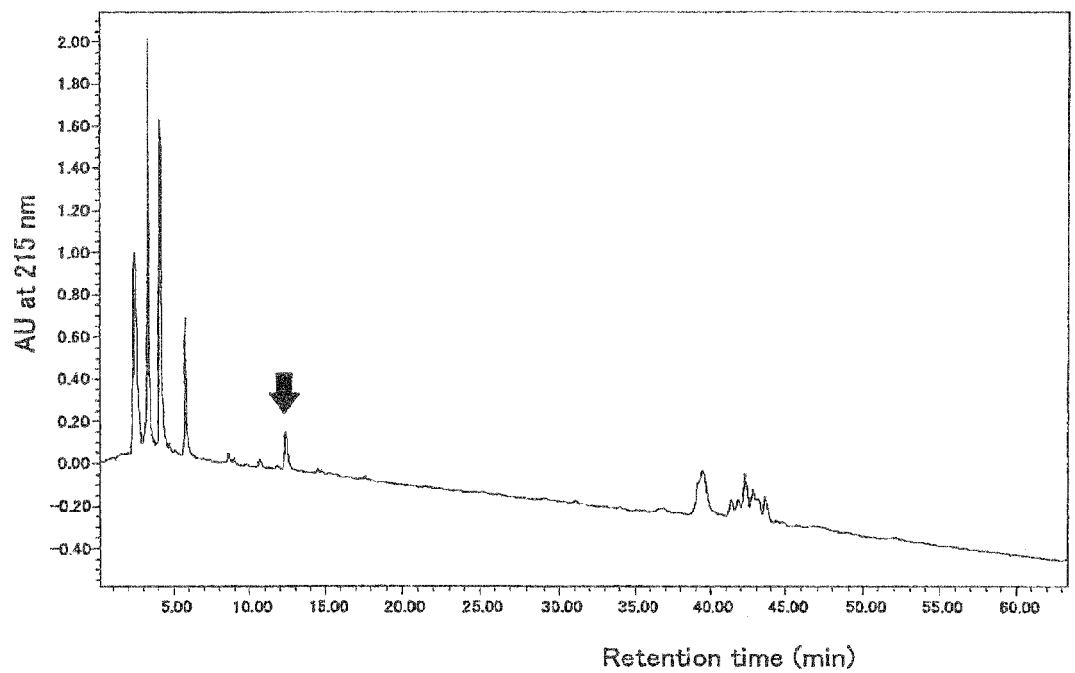
FIG. 1 shows a separation chromatogram of a water-soluble peptide fraction obtained from Gouda cheese as a raw material (Example 1).
Figure 2:
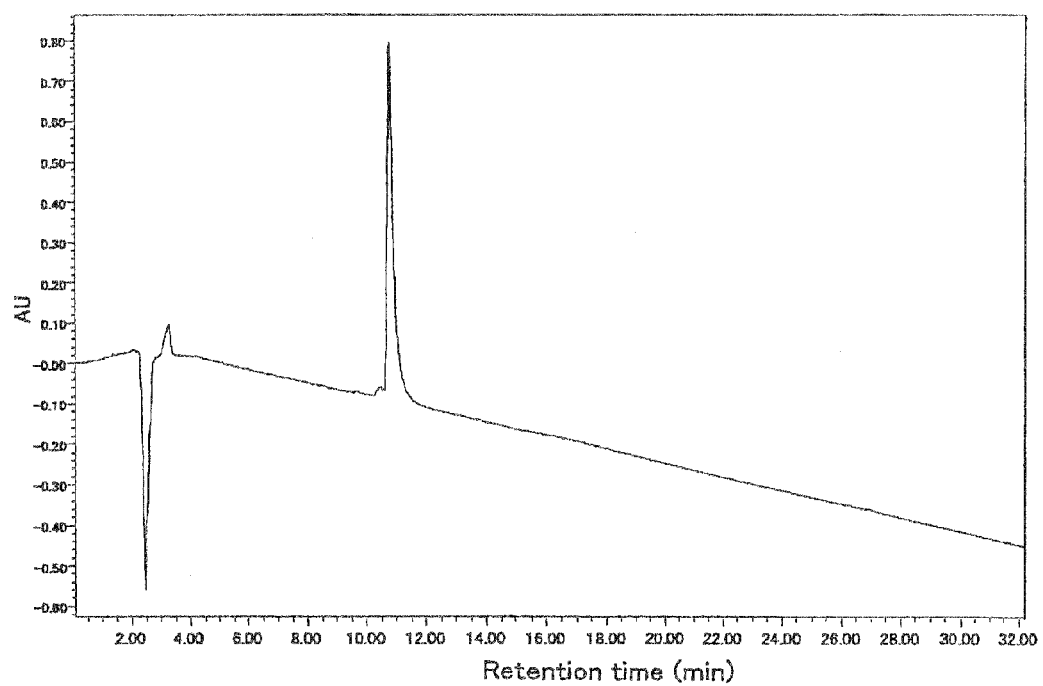
FIG. 2 shows a separation chromatogram of a synthetic peptide fraction (Example 2).

[FIG. 1] An arrow indicates an amino acid sequence (His-Pro-Ile-Lys-His-Gln-Gly-Leu-Pro-Gln SEQ ID NO: 1) according to the present invention.

Figure 4:
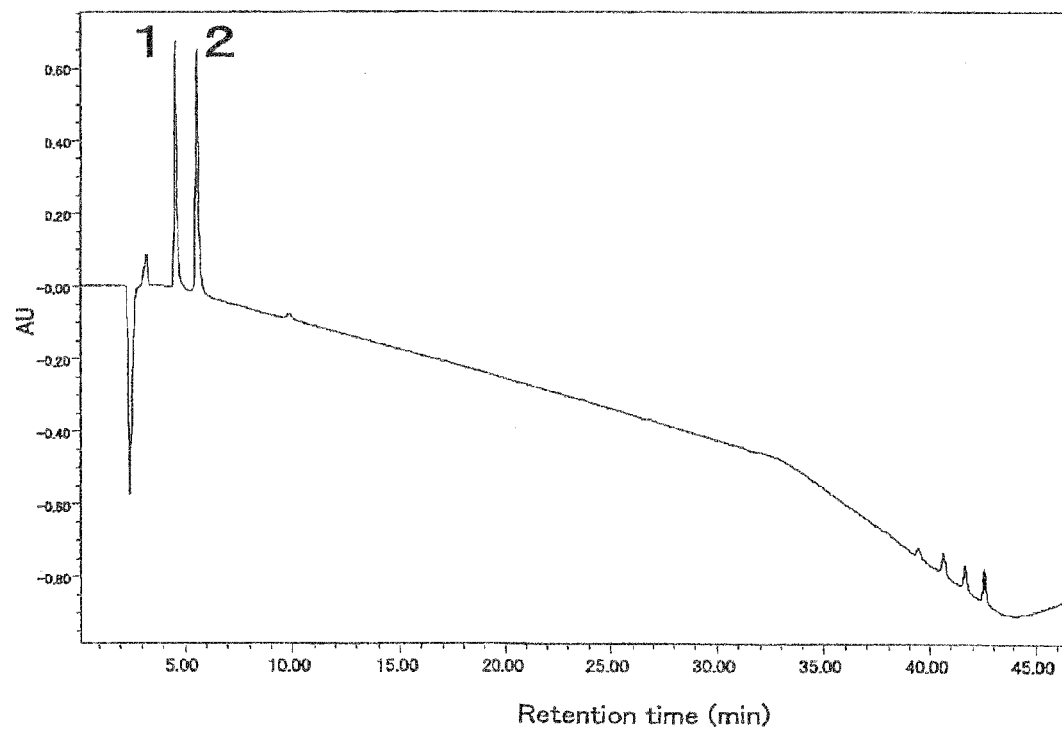
FIG. 4 shows a separation chromatogram of a tryptic peptide fraction (Example 3).

[FIG. 4] Reference numeral 1 indicates an amino acid sequence (His-Pro-Ile-Lys SEQ ID NO: 2) according to the present invention, and reference numeral 2 indicates an amino acid sequence (His-Gln-Gly-Leu-Pro-Gln SEQ ID NO: 3) according to the present invention.

Figure 5:
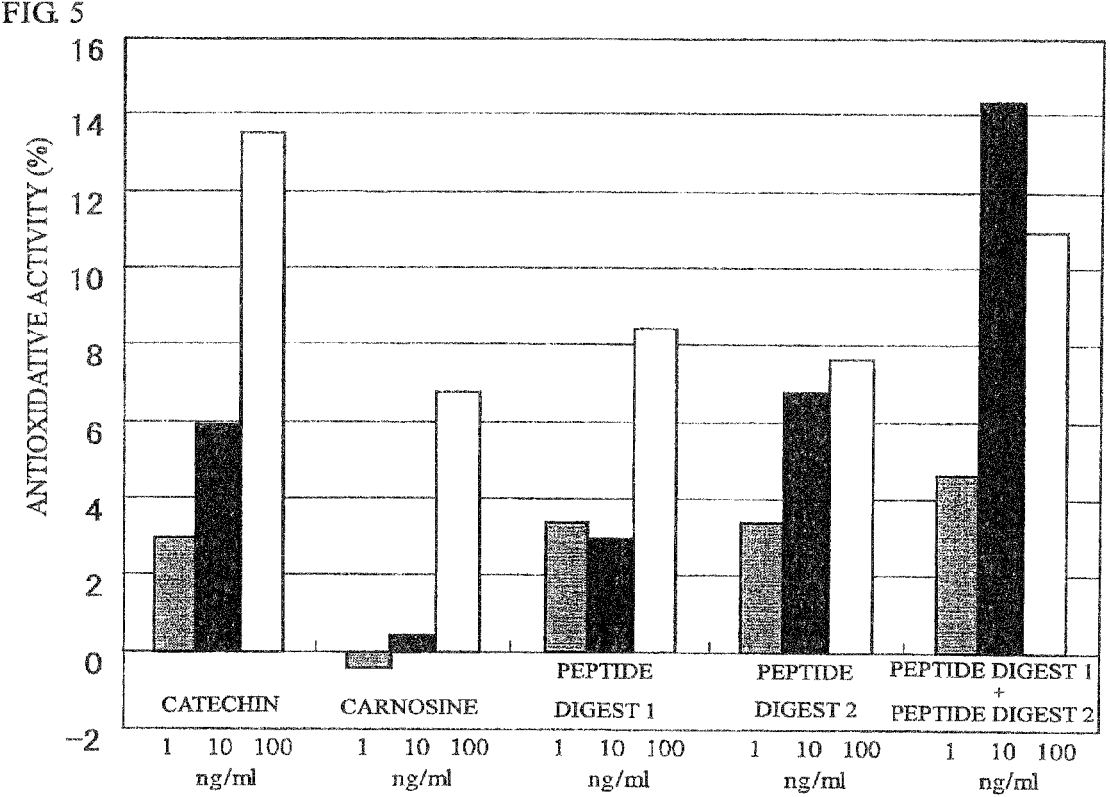
FIG. 5 shows antioxidation activity evaluation results for a tryptic peptide fraction (Example 3 and Test Example 3).

[FIG. 5] A peptide digest 1 indicates an amino acid sequence (His-Pro-Ile-Lys SEQ ID NO: 2) according to the present invention, and a peptide digest 2 indicates an amino acid sequence (His-Gln-Gly-Leu-Pro-Gln SEQ ID NO: 3) according to the present invention.

BEST MODE FOR CARRYING OUT THE INVENTION

The peptide consisting of an amino acid sequence shown by His-Pro-Ile-Lys-His-Gln-Gly-Leu-Pro-Gln (SEQ ID NO: 1), His-Pro-Ile-Lys (SEQ ID NO: 2), or His-Gln-Gly-Leu-Pro-Gln (SEQ ID NO: 3) that may be used in the present invention may be obtained by suspending cheese in a solvent, defatting the suspension, and removing an insoluble substance by centrifugation. Proteins may be removed from the resulting fraction. The expression "suspending cheese in a solvent" used in the present invention refers to adding a solvent to cheese and homogenizing the mixture or crushing the cheese in the solvent so that the cheese has a size that allows a water-soluble peptide fraction to be easily obtained. As the solvent, an aqueous solvent such as water or a phosphate buffer may be used. The fraction may then be desalted using a permeable membrane, an ion-exchange resin, or the like, or may be dried by freeze drying, spray drying, or the like to obtain a powder.

As the raw material cheese used to obtain the peptide consisting of an amino acid sequence shown by the formula (1), (2), or (3), or the raw material cheese used to obtain the blood adiponectin level increase acceleration and/or decrease inhibition agent or the blood adiponectin level increase acceleration and/or decrease inhibition food or drink according to the present invention that includes a component contained in cheese as an active ingredient, natural cheese such as Parmesan cheese, Gruyere cheese, Maribo cheese, Gouda cheese, cheddar cheese, Emmental cheese, Edam cheese, Camembert cheese, Brie cheese, Munster cheese, Pont l'Évêque cheese, Stilton cheese, Danablu cheese, or blue cheese, processed cheese produced using such natural cheese as a raw material, or the like may be used. It is desirable to use lactic acid-fermented natural cheese having a high degree of maturation in order to obtain the peptide consisting of an amino acid sequence shown by the formula (1), (2), or (3). The above-mentioned cheese may be used directly, or a fraction obtained by suspending the cheese in a solvent, defatting the suspension, removing an insoluble substance, and removing proteins may be used. A fraction obtained by purifying the resulting fraction using a permeable membrane or by chromatography (e.g., gel permeation chromatography or ion-exchange chromatography) may be used. The fraction may be concentrated or dried before use.

The fraction that is obtained by suspending the cheese in a solvent, defatting the suspension, removing an insoluble substance, and removing proteins and contains the peptide consisting of an amino acid sequence shown by the formula (1), (2), or (3) may be purified by reverse phase chromatography using a C18 column. When allowing the fraction containing the peptide according to the present invention to pass through a C18 column under acidic conditions (e.g., trifluoroacetic acid (TFA)) or under neutral conditions (e.g., distilled water), a fraction having an antioxidative activity is mainly separated into a permeable fraction that is not adsorbed on the column and a fraction that is adsorbed on the column and eluted with 80% acetonitrile.

After dissolving the fraction containing the peptide in distilled water, the solution is subjected to reverse phase HPLC using a YMC-Pack ODS-A column (4.6 mm×150 mm: manufactured by YMC) to fractionate the peptide. It is desirable to carry out chromatography at a flow rate of 0.8 ml/min and a detection wavelength of 215 nm using a solvent containing a liquid A (50 mM ammonium acetate aqueous solution) and a liquid B (80% acetonitrile) at a concentration gradient of 12% B→60% B (60 min).

The peptide according to the present invention consisting of an amino acid sequence shown by the formula (1), (2), or (3) and the fraction containing the peptide may be added to food or drink to prevent a deterioration in the quality of the food or drink. When adding the peptide or the fraction containing the peptide to food or drink, a water-soluble peptide obtained by milling cheese in water, defatting the cheese, removing an insoluble substance by centrifugation, and removing proteins may be added to the food or drink, or a product obtained by desalting the peptide using a permeable membrane, an ion-exchange resin, or the like, or a powder obtained by drying the peptide by freeze drying, spray drying, or the like, may be added to the food or drink. A synthetic peptide may also be used.

The peptide according to the present invention that consists of an amino acid sequence shown by the formula (1), (2), or (3) and has an antioxidative effect and the fraction containing the peptide may be administered orally or parenterally to remove active oxygen, free radicals, and the like in vivo so that the progress of disease, aging, and the like can be prevented. The peptide according to the present invention that consists of an amino acid sequence shown by the formula (1) and has an adiponectin production promotion effect and the fraction containing the peptide may be administered orally or parenterally to promote adiponectin production in vivo so that arteriosclerosis can be suppressed, and fat burning in the liver and the muscle can be promoted. When administering the peptide or the fraction containing the peptide orally or parenterally, the dosage form of the peptide according to the present invention that has an antioxidative effect or an adiponectin production promotion effect, or the blood adiponectin level increase acceleration and/or decrease inhibition agent including a component contained in cheese as an active ingredient may be an oral administration preparation such as a tablet, a capsule, a granule, a powder, a pill, a troche, a sublingual agent, or a liquid medicine, or may be a parenteral administration preparation such as an injection or a suppository.

The oral dosage of the peptide according to the present invention that consists of an amino acid sequence shown by the formula (1), (2), or (3) and has an antioxidative effect, or the peptide according to the present invention that consists of an amino acid sequence shown by the formula (1) and has an adiponectin production promotion effect may be appropriately determined taking into consideration the objective of treatment or prevention, symptom, weight, age, sex, and the like. An effect of suppressing oxidative disorder due to active oxygen, free radicals, or the like that adversely affects disorder, aging, and the like, or an effect of promoting adiponectin production can be obtained by normally administering the peptide that consists of an amino acid sequence shown by the formula (1), (2), or (3) and has an antioxidative effect, or the peptide that consists of an amino acid sequence shown by the formula (1) and has an adiponectin production promotion effect in an amount of 10 µg to 500 mg per day (adult). The present invention is thus effective at a low dosage.

The dosage of the blood adiponectin level increase promotion and/or decrease inhibition agent or the blood adiponectin level increase promotion and/or decrease inhibition food or drink according to the present invention that includes a component contained in cheese as an active ingredient may be appropriately determined taking into consideration the objective of treatment or prevention, symptom, weight, age, sex, and the like. The blood adiponectin level increase promotion and/or decrease inhibition agent or the blood adiponectin level increase promotion and/or decrease inhibition food or drink is normally administered so that the intake (adult) of the active ingredient corresponds to about 20 to 200 g of the cheese.

The peptide according to the present invention consisting of an amino acid sequence shown by the formula (1), (2), or (3) exhibits an antioxidative effect or an adiponectin production promotion effect in vivo through oral ingestion of a food, drink, or feed that contains the peptide, and prevents a deterioration in the food, drink, or feed due to oxidation.

The blood adiponectin level increase promotion and/or decrease inhibition agent or the blood adiponectin level increase promotion and/or decrease inhibition food or drink according to the present invention includes a component contained in cheese as an active ingredient. The blood adiponectin level increase promotion and/or decrease inhibition agent or the blood adiponectin level increase promotion and/or decrease inhibition food or drink according to the present invention includes a blood adiponectin level increase promotion and/or decrease inhibition component contained in cheese.

Examples of the antioxidation or adiponectin production promotion food or drink according to the present invention or the blood adiponectin level increase promotion and/or decrease inhibition food or drink that includes a component contained in cheese as an active ingredient include cheese, butter, milk-based drinks, soft drinks, juice, yogurt, jelly, bread, ice cream, noodles, sausage, snacks, cake, pudding, sausage, modified milk for children, baby food, and the like.

The peptide according to the present invention that consists of an amino acid sequence shown by the formula (1), (2), or (3) and has an antioxidative effect may be used as an antioxidant that includes only one type of peptide as an active ingredient, or an antioxidative food, drink, or feed that includes only one type of peptide. Note that an antioxidant that includes one or more types of peptides as an active ingredient, or an antioxidative food, drink, or feed that includes one or more types of peptides may be prepared.

The present invention is described in more detail below by way of examples and test examples, which are given for the purpose of illustration and should not be construed as limiting the present invention.

EXAMPLE 1

Preparation of Gouda Cheese Peptide 160 ml of distilled water was added to 40 g of Gouda cheese. After milling the Gouda cheese using a Waring blender (manufactured by Nihonseiki Kaisha Ltd.) for 15 minutes, the resulting product was crushed for 30 seconds using a Polytron homogenizer (manufactured by Kinematica). After removing milk fat produced during crushing, insoluble components were removed from the resulting cheese slurry by centrifugation (6000×g, 20 min, 4° C.). The supernatant liquid was then filtered through a filter paper (No. 113; manufactured by Whatman). After the addition of ethanol to the resulting filtrate to a concentration of 70%, the mixture was allowed to stand overnight at 4° C. After removing insoluble components by centrifugation (9000×g, 20 min, 4° C.), ethanol was removed using an evaporator. The resulting product was freeze-dried to obtain a water-soluble Gouda cheese peptide fraction.

After dissolving the water-soluble peptide fraction in distilled water, the solution was subjected to reverse phase HPLC using a YMC-Pack ODS-A column (4.6 mm×150 mm: manufactured by YMC) to obtain a purified water-soluble peptide fraction. Chromatography was carried out at a flow rate of 0.8 ml/min and a detection wavelength of 215 nm using a solvent containing a liquid A (50 mM ammonium acetate aqueous solution) and a liquid B (80% acetonitrile) at a concentration gradient of 12% B→60% B (60 min). The results are shown in FIG. 1. The antioxidative activity of the fraction was measured using a method described in Test Example 1. A strong antioxidative activity (see arrow) was observed in the chromatogram.

The molecular weight of the resulting Gouda cheese peptide was estimated using a liquid chromatography-mass spectrometer (manufactured by Nippon Thermo Co., Ltd.). The amino acid sequence was analyzed using a peptide sequencer (manufactured by Applied Biosystems). It was confirmed that the amino acid sequence indicated by the arrow in FIG. 1 was His-Pro-Ile-Lys-His-Gln-Gly-Leu-Pro-Gln (SEQ ID NO: 1).

The peptide thus obtained can be utilized directly as the antioxidant or the adiponectin production promoter according to the present invention.

TEST EXAMPLE 1

Measurement of Antioxidative Activity of Peptide

The antioxidative activity of the peptide fractionated in Example 1 was measured utilizing the β-carotene degradation effect of an oxide of linoleic acid. Specifically, a 300 ml Erlenmeyer flask was charged with 0.5 ml of a β-carotene solution (1 mg/ml chloroform), 0.2 ml of a linoleic acid solution (100 mg/ml chloroform), and 1.0 ml of a Tween 40 solution (200 mg/ml chloroform). After completely removing chloroform using nitrogen gas, 100 ml of distilled water was added to dissolve the components. 9.0 ml of a 0.2 M phosphate buffer (pH: 7.0) was then added to the solution to prepare a linoleic acid-β-carotene solution. 0.18 ml of the linoleic acid-β-carotene solution was added to a 98-well microwell plate to which 0.02 ml of the peptide fraction was provided. The absorbance $S_0$ at 490 nm was measured immediately after the addition. When preparing the linoleic acid-β-carotene solution, the amount of the β-carotene solution was appropriately adjusted so that the absorbance $S_0$ was about 1.2 (1.1 to 1.3). The microwell plate was placed in a thermostat bath at 50° C. immediately after measuring the absorbance $S_0$, and the peptide fraction was incubated for 30 minutes. The absorbance $S_{30}$ was measured immediately after incubation. A decrease ($\Delta S = S_0 - S_{30}$) in absorbance at 490 nm over 30 minutes was then calculated. 70% ethanol was used as a blank instead of the sample and subjected to the above operation. Specifically, the absorbance $B_0$ immediately after adding the linoleic acid-β-carotene solution and the absorbance $B_{30}$ after being kept at 50° C. for 30 minutes were measured, and a decrease ($\Delta B = B_0 - B_{30}$) in absorbance at 490 nm over 30 minutes was calculated. The antioxidative activity (antioxidation rate (%)) was determined by substituting the resulting values in the following expression.

Antioxidation rate (%) = $[\Delta B - \Delta S]/(\Delta B) \times 100$

As a positive control, carnosine (β-Ala-L-His; manufactured by Peptide Institute, Inc.) (muscle-derived antioxidative peptide) prepared to a concentration of 0.01 µg/ml, 0.1 µg/ml, or 1 µg/ml was used.

Table 1 shows the antioxidative activity measurement results for the purified peptide and carnosine (positive control).

TABLE 1

| | Antioxidative activity (%) | | |
|---|---|---|---|
| | Sample concentration (µg/ml) | | |
| | 0.01 | 0.1 | 1 |
| Carnosine (Ala-His) | 32.9 | 57.8 | 78.3 |
| His-Pro-Ile-Lys-His-Gln-Gly-Leu-Pro-Gln (SEQ ID NO: 1) | 13.0 | 41.0 | 64.6 |

As shown in Table 1, a concentration-dependent antioxidative activity was observed when adding the peptide.

As is clear from the results obtained in this test example, it was found that the cheese-derived peptide consisting of an amino acid sequence shown by His-Pro-Ile-Lys-His-Gln-Gly-Leu-Pro-Gln (SEQ ID NO: 1) had antioxidative activity (radical scavenger activity), and is useful for preventing or treating oxidative cell disorder due to active oxygen and lipid peroxides.

EXAMPLE 2

Synthesis of Peptide

A peptide consisting of an amino acid sequence shown by the formula (1) was synthesized using a peptide synthesizer. A linear protected peptide was synthesized (0.25 mmol) using a peptide synthesizer 431A (manufactured by Applied Biosystems) by sequentially extending the peptide chain from the C-terminal using a 9-fluorenylmethyloxycarbonyl (Fmoc) group as the amino terminal protecting group utilizing a p-hydroxymethylphenoxymethylpolystyrene (HMP) resin. An HMP resin-bonded protected peptide was thus obtained. The peptide was separated from the HMP resin and the protecting group was removed using trifluoroacetic acid (TFA) in the presence of phenol, 1,2-ethanedithiol, and thioanisole. After removing TFA by concentration under reduced pressure, the unpurified peptide was crystallized from ethyl ether, dissolved in 5% acetic acid, and freeze-dried.

The resulting unpurified linear peptide was subjected to HPLC using a YMC-Pack ODS-A column (manufactured by YMC; 4.6×150 mm). Chromatography was carried out at a flow rate of 0.8 ml/min and a detection wavelength of 215 nm using a solvent containing a liquid A (50 mM ammonium acetate aqueous solution) and a liquid B (80% acetonitrile) at a concentration gradient of 12% B→60% B (60 min). The purity of the resulting purified linear peptide was 98% as a result of HPLC analysis. The results are shown in Table 2.

The peptide thus obtained can be utilized directly as the antioxidant or the adiponectin production promoter according to the present invention.

TEST EXAMPLE 2

Measurement of Antioxidative Activity of Synthetic Peptide

Figure 3:
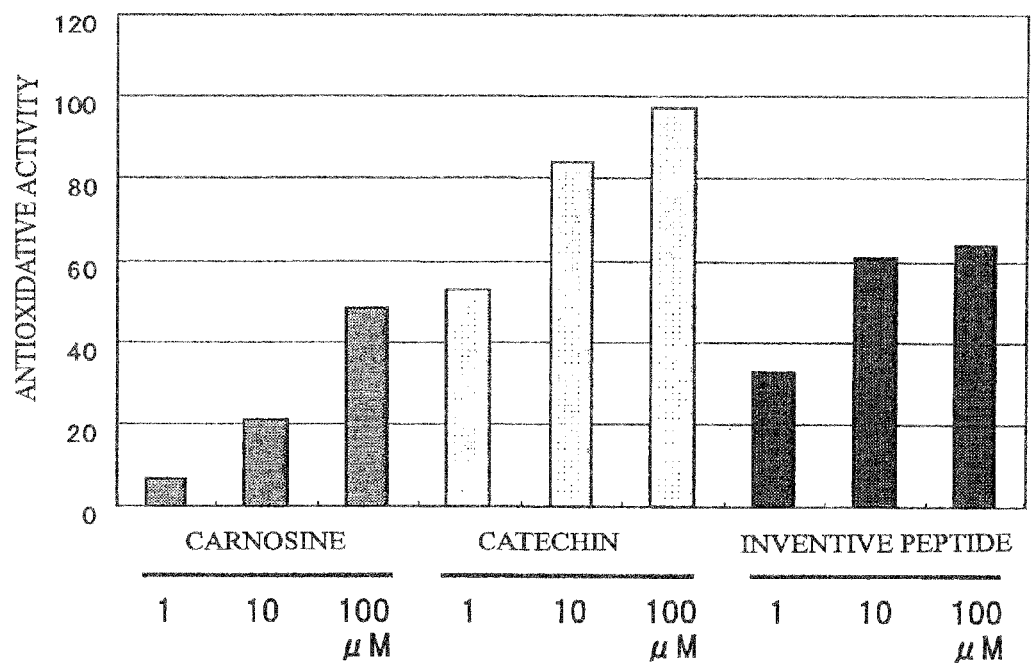
FIG. 3 shows antioxidation activity evaluation results for a synthetic peptide fraction (Example 2 and Test Example 2).

The antioxidative activity of the peptide obtained in Example 2 was measured in the same manner as in Test Example 1. As a positive control, carnosine (β-Ala-L-His; manufactured by Peptide Institute, Inc.) (muscle-derived antioxidative peptide) and catechin (manufactured by Wako Pure Chemical Industries, Ltd.) (1 μm, 10 μm, or 100 μm) were used. Table 2 and FIG. 3 show the evaluation results for the antioxidative activity of the synthetic peptide. As shown in Table 2 and FIG. 3, it was confirmed that the resulting synthetic peptide had strong antioxidative activity.

TABLE 2

| | Antioxidative activity (%) | | |
|---|---|---|---|
| | Sample concentration (μg/ml) | | |
| | 1 | 10 | 100 |
| Catechin | 52.65 | 84.45 | 97.17 |
| Carnosine | 7.07 | 21.2 | 48.41 |
| Synthetic peptide | 32.86 | 61.13 | 63.6 |

EXAMPLE 3

Preparation of Tryptic Digest

A tryptic digest of the peptide obtained in Example 2 was prepared.

The peptide obtained in Example 2 and trypsin (manufactured by Sigma-Aldrich Japan K.K.) were dissolved in an enzyme reaction solution (50 mM Tris-HCl, 20 mM $CaCl_2$, pH: 8.0) to a concentration of 1 mg/ml, respectively. 5 μl of a trypsin solution was added to 500 μl of a peptide solution, and the mixture was allowed to react at 37° C. for two hours. After the addition of 5 μl of a trypsin solution, the mixture was allowed to react at 37° C. for 18 hours to obtain a tryptic digest.

The tryptic digest was dissolved in distilled water, and then subjected to HPLC using a YMC-Pack ODS-A column (manufactured by YMC; 4.6×150 mm). The HPLC analysis was conducted under the same conditions as those for the peptide before trypsin digestion in Example 2. The results are shown in FIG. 4. As shown in FIG. 4, two peaks were observed.

Two fragments (His-Pro-Ile-Lys (SEE ID NO: 2), peptide 1) and (His-Gln-Gly-Leu-Pro-Gln (SEQ ID NO: 3), peptide 2) corresponding to two peaks decomposed by trypsin were collected ten times, and dried using a centrifugal evaporator to obtain two peptides (i.e., tryptic digests). The antioxidative activities of the resulting two peptides and the tryptic digest before fractionation were measured using a method of Test Examples 3. As shown in FIG. 5, it was confirmed that the synthetic peptide had strong antioxidative activity.

The antioxidative peptide thus obtained can be utilized directly as the antioxidant according to the present invention.

TEST EXAMPLE 3

Measurement of Antioxidative Activity of Peptide

The antioxidative activities of the two peptides (i.e., tryptic digests) obtained in Examples 3 and the tryptic digest before fractionation were measured using a carotene degradation method in the same manner as in Test Example 2. The peptide concentration was determined by dissolving each peptide in 500 μl of pure water and measuring the peptide concentration using a Micro BCA Protein assay kit (manufactured by Pierce). As a positive control, carnosine (β-Ala-L-His; manufactured by Peptide Institute, Inc.) and catechin (manufactured by Wako Pure Chemical Industries, Ltd.) were used in the same manner as in Test Example 2. A diluted solution (1 ng/ml, 10 ng/ml, and 100 ng/ml) was prepared for each fragment, and the antioxidative activity was evaluated using the β-carotene degradation method. FIG. 5 shows the evaluation results for the antioxidative activity of the peptide as the tryptic digest. As shown in FIG. 5, it was confirmed that the peptide as the tryptic digest had strong antioxidative activity.

TEST EXAMPLE 4

Peptide Adipocyte Administration Experiment

Experiments were conducted in which the peptide isolated from the cheese in Example 1 was administered to primary-cultured visceral fat cells.

The experiments were conducted using rat primary-cultured visceral fat cells (VAC01, manufactured by Cell Garage Co., Ltd.) and a visceral fat cytodifferentiation medium (manufactured by Cell Garage Co., Ltd.). Cells preserved in a frozen state in accordance with the protocol provided by Cell Garage Co., Ltd. were melted and disseminated in a 24-well plate (zeroth day). A culture medium (peptide concentration: 100 μM, 50 μM, 10 μM, or 0 μM) in which the synthetic peptide was dissolved was added to the 24-well plate on the second day, fifth day, and seventh day, and the synthetic peptide was cultured. The culture supernatant liquid was collected on the fifth day, seventh day, and eighth day to measure the adiponectin level. The cells were collected on the eighth day. The enzyme activity of glycerol-3-phosphate dehydrogenase (GPDH) in the cells, the DNA content of each well, and the intracellular fat accumulation level were measured. GPDH is an enzyme that functions when triglyceride is synthesized from glucose to produce mature fat cells. In this example, preadipocytes were differentiated, and the effect of administration of the peptide according to the present invention was observed.

The DNA content was determined using a DNA quantization kit (manufactured by Cell Garage Co., Ltd.).

The glycerol-3-phosphate dehydrogenase (GPDH) enzyme activity in the cells was measured using a GPDH activity measurement kit (manufactured by Cell Garage Co., Ltd.) in accordance with the protocol provided by Cell Garage Co., Ltd. The measurement results were standardized by the content of DNA extracted from each well.

The adiponectin level in the culture supernatant liquid was measured using an adiponectin ELISA kit (manufactured by Otsuka Pharmaceutical Co., Ltd.). The measurement results were standardized by the content of DNA extracted from each well.

The intracellular fat accumulation was determined by fat staining with oil red O and absorbance measurement using a fat staining kit (manufactured by Cell Garage Co., Ltd.).

Peptide Adipocyte Administration Experiment Results

A cell-derived DNA in each well was measured. In the Student t-test, a significant difference in cell DNA content was not observed between the group to which the peptide according to the present invention was added and the group to which the peptide according to the present invention was not added.

The GPDH activity (per unit DNA content) was measured. The group to which the peptide according to the present invention was added (10 or 50 μM) exhibited GPDH activity (standardized by the cell DNA content of each well) significantly higher than that of the group to which the peptide according to the present invention was not added. A significant difference was not observed between the group to which the peptide according to the present invention was added in an amount of 100 μM and the group to which the peptide according to the present invention was not added.

Figure 6:
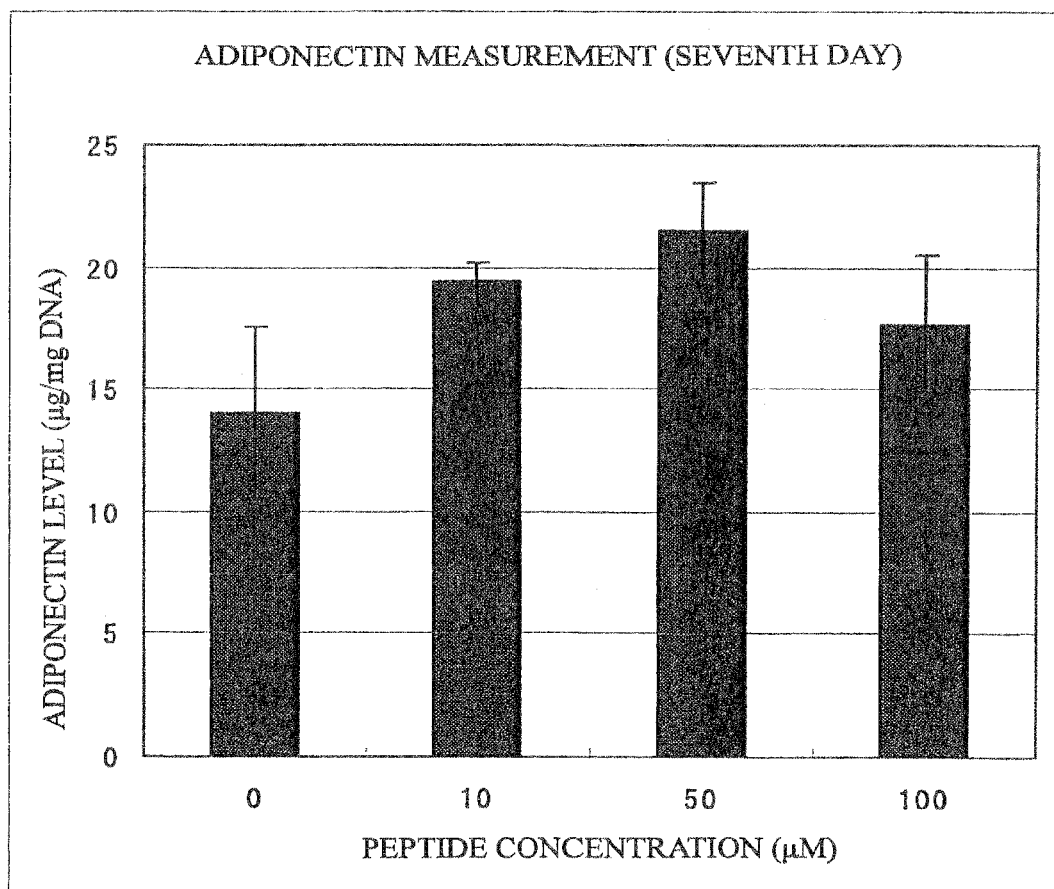
FIG. 6 shows the production of adiponectin (per unit DNA content) corresponding to different peptide concentrations (Example 1 and Test Example 4).

According to the measurement results for a change in adiponectin level with respect to the number of incubation days, production of adiponectin was maximized on the seventh day, but quickly decreased on the eighth day. FIG. 6 shows the difference in production of adiponectin (per unit DNA content) due to the difference in peptide concentration on the seventh day when the adiponectin level in the culture supernatant liquid was the highest.

The cells to which the peptide was added produced significantly more adiponectin than the cells cultured without adding the peptide. This tendency was significantly marked for the cells to which the peptide was added at a concentration of 10 or 50 μM. The above results indicate that the cheese-derived peptide is a component that exhibits an adiponectin level increase promotion and/or decrease inhibition effect.

The active ingredient that exhibits the adiponectin level increase promotion and/or decrease inhibition effect according to the present invention is not limited to these peptides, but is considered to include various other active ingredients.

Figure 7:
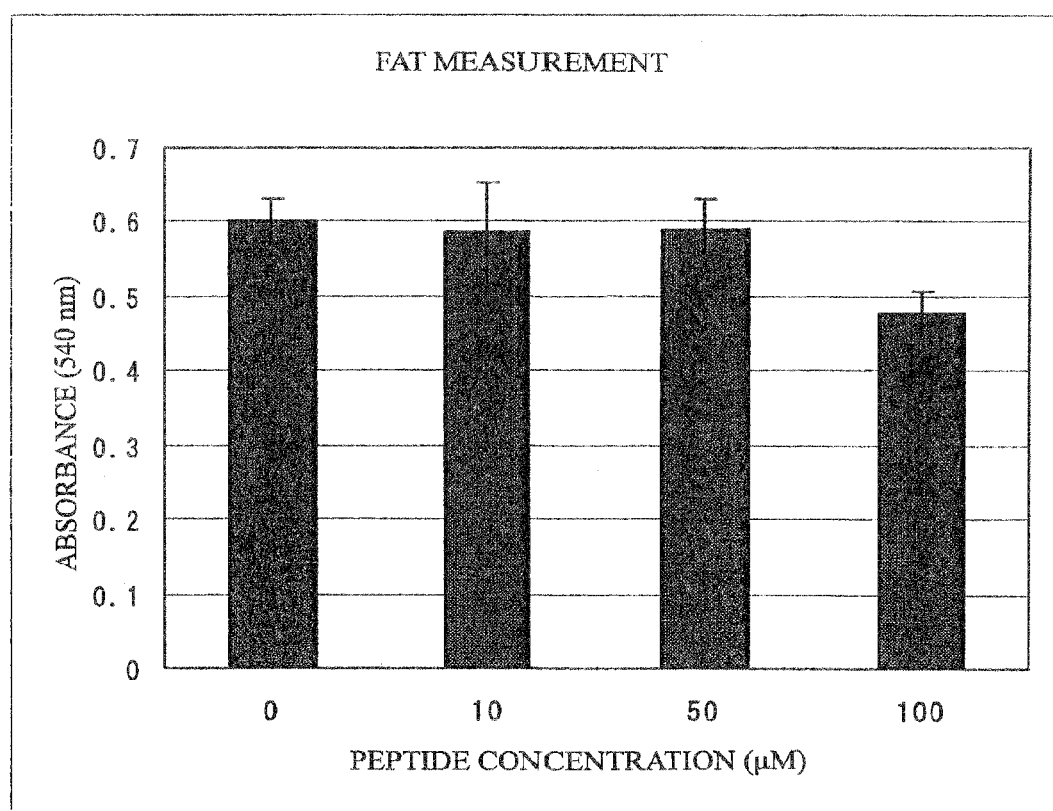
FIG. 7 shows the amount of fat accumulation corresponding to different peptide concentrations (Example 1 and Test Example 4).

FIG. 7 shows the fat accumulation determination results on the eighth day stain utilizing fat staining with oil red 0 and absorbance measurement.

Since the adipocytes must be fixed for staining, the number of cells (cell DNA content) of the well subjected to fat determination cannot be determined. However, since the number of cells was not affected by the addition of the peptide from the DNA quantization results of the cells cultured under the same conditions, it is considered that almost the same number of cells are present in each well. In the Student t-test, a significant difference in fat accumulation was not observed between the cells cultured without adding the peptide and the cells to which the peptide was added. The fat accumulation decreased to only a small extent for the cells to which 100 μM of the peptide was added.

Summary of Peptide Adipocyte Administration Experiment

When the peptide according to the present invention was added to fat precursor cells in an amount of 10 to 50 μM and cultured, (1) the GPDH activity increased, (2) the production of adiponectin increased, and (3) the amount of fat accumulation did not change.

In this case, it is considered that differentiation from fat precursor cells to fat cells was promoted by the addition of the peptide, or the steatogenesis activity in the differentiated mature fat cells was promoted. However, since there was no difference in the amount of fat accumulation from the cells to which the peptide was not added, it may be considered that the synthesized fat was decomposed by another molecular mechanism. Adiponectin is a beneficial cytokine secreted from the mature fat cells. It was confirmed that the peptide according to the present invention exhibited an adiponectin production promoting effect. Therefore, it was confirmed that the peptide according to the present invention had an effect of increasing the production of adiponectin by promoting functional differentiation from fat precursor cells to fat cells, and may suppress fat accumulation in the cells.

It is considered that adiponectin has an effect of promoting fat burning in the liver and muscle in addition to arteriosclerosis inhibitory activity. The peptide according to the present invention is considered to produce fat cells that easily produce adiponectin to prevent metabolic syndrome.

When the peptide according to the present invention was added to fat precursor cells in an amount of 100 μM and cultured, (1) the GPDH activity did not change, (2) the production of adiponectin increased, and (3) the amount of fat accumulation did not change (no significant difference was observed, but a tendency to decrease was observed).

These results suggest that the effect of the peptide according to the present invention on fat cells differs depending on the concentration (i.e., an optimum concentration exists). It was confirmed that the production of adiponectin was promoted by adding the peptide according to the present invention. It was also confirmed that the peptide according to the present invention exhibited a fat accumulation inhibition effect. This suggests that the peptide according to the present invention has an effect of preventing metabolic syndrome.

It was also confirmed that the peptide consisting of an amino acid sequence shown by His-Pro-Ile-Lys (SEQ ID NO: 2) or His-Gln-Gly-Leu-Pro-Gln (SEQ ID NO: 3) (i.e., tryptic product of the peptide consisting of an amino acid sequence shown by His-Pro-Ile-Lys-His-Gln-Gly-Leu-Pro-Gln SEQ ID NO: 1) had a similar adiponectin production promotion effect.

EXAMPLE 4

Preparation of Bacteria-Ripened Cheese

Raw material milk was sterilized at 75° C. for 15 seconds, and cooled to 30° C. Then, 0.01% calcium chloride was added to the raw material milk. After the addition of 1.5% of a commercially available lactic acid bacteria starter (manufactured by Christian Hansen) for producing cheese and 3% of *Lactobacillus helveticus* SBT2171 (FERM P-14381), 0.003% of rennet was added to coagulate the milk. The resulting curdle was cut and stirred until the pH became 6.1 to 6.2. The whey was then discharged to obtain curds. The curds were placed in a mold and then compressed. After the addition of salt, the resulting product was ripened at 10° C. to obtain Gouda-type hard natural cheese. The hard natural cheese (ripened for 12 months) was minced using a mincing machine ("GM-DX" manufactured by Nippon Career Industry Co., Ltd.), and then freeze-dried. The resulting product was ground using a coffee mill to obtain a cheese powder.

TEST EXAMPLE 5

Check on Blood Adiponectin Level Increase Acceleration and/or Decrease Inhibition Effect A blood adiponectin level increase acceleration and/or decrease inhibition effect was checked using the cheese powder obtained in Example 4. An animal experiment was conducted (one group=eight animals). A high-fat feed containing the cheese powder was fed to one group (cheese feed group), and a control feed was fed to another group (control feed group) instead of the high-fat feed containing the cheese powder. The control feed contained milk casein as a protein source and a butter oil as a lipid source. The control feed was prepared so that the content of common components, main minerals, and vitamin E (α-tocopherol) was the same as that of the high-fat feed containing the cheese powder based on the component analysis results for the cheese (see Table 3). In the high-fat feed containing the cheese powder, proteins and lipids other than the cheese component were not used.

TABLE 3

| Cheese components | |
|---|---|
| Protein | 44.8 g/100 g |
| Fat | 43.4 g/100 g |
| Ash | 6.3 g/100 g |
| Sodium | 1050 mg/100 g |
| Potassium | 130 mg/100 g |
| Calcium | 1190 mg/100 g |
| Magnesium | 41 mg/100 g |
| Phosphorus | 850 mg/100 g |
| Iron | 0.22 mg/100 g |
| α-Tocopherol | 0.9 mg/100 g |

The control feed was fed to each group for four weeks, and the control feed or the high-fat feed containing the cheese powder was then fed to the respective groups for four weeks. Blood was collected in the fourth week and the eighth week, and the blood adiponectin level was measured using a mouse/rat adiponectin ELISA kit (manufactured by Otsuka Pharmaceutical Co., Ltd.). The blood triglyceride level and the total blood cholesterol level were measured in the eighth week.

The results are shown in Tables 4 and 5. As shown in Tables 4 and 5, while the blood adiponectin level of the control feed group decreased with the passage of time, the blood adiponectin level of the cheese feed group increased with the passage of time. Specifically, it was confirmed that the blood adiponectin level increased or a decrease in blood adiponectin level was suppressed due to ingestion of the cheese. The blood triglyceride level of the cheese feed group significantly decreased as compared with the control feed group. The total blood cholesterol level of the cheese feed group tended to decrease, although no significant difference was observed.

TABLE 4

| | Blood adiponectin level (μg/ml) | | |
|---|---|---|---|
| Feed | Four weeks | Eight weeks | Change rate (%) |
| Control feed group | 11.19 | 10.40 | 93.72 |
| Cheese feed group | 10.41 | 13.14 | 129.67 |

TABLE 5

| Feed | Triglyceride level (mg/dl) | Total cholesterol level (mg/dl) |
|---|---|---|
| Control feed group | 111.75 | 80.38 |
| Cheese feed group | 75.63 | 68.63 |

EXAMPLE 5

Production of Tablet 20 wt% of the antioxidative peptide (His-Pro-Ile-Lys-His-Gln-Gly-Leu-Pro-Gln SEQ ID NO: 1) obtained in Example 1, 46 wt% of lactose (manufactured by DMV), 31 wt% of crystalline cellulose (manufactured by Wako Pure Chemical Industries, Ltd.), and 3 parts by weight of water were thoroughly mixed. The mixture was tableted using a tableting machine (manufactured by Fuji Yakuhin Kikai Co., Ltd.) to obtain antioxidative tablets according to the present invention.

EXAMPLE 6

Production of Fruit Juice Drink

Each component was mixed according to the formulation shown in Table 6. After charging a container with the mixture, the mixture was sterilized by heating to obtain an antioxidative fruit juice drink according to the present invention containing the synthetic antioxidative peptide (His-Pro-Ile-Lys-His-Gln-Gly-Leu-Pro-Gln SEQ ID NO: 1) obtained in Example 2 of the present invention.

TABLE 6

| Mixed isomerized sugar | 15.4 wt % |
|---|---|
| Fruit juice | 10.0 wt % |
| Citric acid | 0.5 wt % |
| Antioxidative peptide (His-Pro-Ile-Lys-His-Gln-Gly-Leu-Pro-Gln) SEQ ID NO: 1) | 0.1 wt % |
| Essence | 0.2 wt % |
| Water | 73.8 wt % |

EXAMPLE 7

Production of Soft Drink

Each component was mixed according to the formulation shown in Table 7. After charging a container with the mixture, the mixture was sterilized by heating to obtain an antioxidative soft drink according to the present invention containing the tryptic peptide (His-Gln-Gly-Leu-Pro-Gln SEQ ID NO: 3) obtained in Example 3 of the present invention.

TABLE 7

| Maltitol | 7.5 wt % |
|---|---|
| 50% lactic acid solution | 0.12 wt % |
| Antioxidative peptide (His-Gln-Gly-Leu-Pro-Gln) SEQ ID NO: 3) | 0.1 wt % |
| Essence | 0.2 wt % |
| Water | 92.08 wt % |

EXAMPLE 8

Production of Soft Drink

Each component was mixed according to the formulation shown in Table 8. After charging a container with the mixture, the mixture was sterilized by heating to obtain an antioxidative soft drink according to the present invention containing the tryptic peptide (His-Gln-Gly-Leu-Pro-Gln SEQ ID NO: 3 and His-Pro-Ile-Lys SEQ ID NO: 2) obtained in Example 3 of the present invention.

TABLE 8

| | |
|---|---|
| Maltitol | 7.5 wt % |
| 50% lactic acid solution | 0.12 wt % |
| Antioxidative peptide (His-Pro-Ile-Lys) SEQ ID NO: 2) | 0.05 wt % |
| Antioxidative peptide (His-Gln-Gly-Leu-Pro-Gln SEQ ID NO: 3) | 0.05 wt % |
| Essence | 0.2 wt % |
| Water | 92.08 wt % |

EXAMPLE 9

Dough was prepared according to the formulation shown in Table 9, formed, and roasted to obtain an antioxidative cookie according to the present invention containing the peptide (His-Pro-Ile-Lys-His-Gln-Gly-Leu-Pro-Gln SEQ ID NO: 1) obtained in Example 1 of the present invention.

TABLE 9

| | |
|---|---|
| Flour | 51.0 wt % |
| Sugar | 20.0 wt % |
| Salt | 0.5 wt % |
| Margarine | 12.5 wt % |
| Egg | 12.5 wt % |
| Water | 2.5 wt % |
| Mineral mixture | 0.8 wt % |
| Antioxidative peptide (Example 1) | 0.2 wt % |

EXAMPLE 10

Each component was mixed according to the formulation shown in Table 10 to obtain an antioxidative dog food according to the present invention containing the antioxidative peptide (His-Pro-Ile-Lys-His-Gln-Gly-Leu-Pro-Gln SEQ ID NO: 1) obtained in Example 1 of the present invention.

TABLE 10

| | |
|---|---|
| Soybean cake | 12.0 wt % |
| Powdered skim milk | 14.9 wt % |
| Soybean oil | 4.0 wt % |
| Corn oil | 2.0 wt % |
| Palm oil | 28.0 wt % |
| Cornstarch | 15.0 wt % |
| Flour | 8.0 wt % |
| Gluten | 2.0 wt % |
| Vitamin mixture | 9.0 wt % |
| Mineral mixture | 2.0 wt % |
| Cellulose | 3.0 wt % |
| Antioxidative peptide (Example 1) | 0.1 wt % |

EXAMPLE 11

Production of Tablet 20 wt % of the antioxidative peptide (His-Pro-Ile-Lys-His-Gln-Gly-Leu-Pro-Gln SEQ ID NO: 1) obtained in Example 1, 46 wt % of lactose (manufactured by DMV), 31 wt % of crystalline cellulose (manufactured by Wako Pure Chemical Industries, Ltd.), and 3 parts by weight of water were thoroughly mixed. The mixture was tableted using a tableting machine (manufactured by Fuji Yakuhin Kikai Co., Ltd.) to obtain adiponectin production promoting tablets according to the present invention.

EXAMPLE 12

Production of Fruit Juice Drink

Each component was mixed according to the formulation shown in Table 11. After charging a container with the mixture, the mixture was sterilized by heating to obtain an adiponectin production promoting fruit juice drink according to the present invention containing the synthetic peptide (His-Pro-Ile-Lys-His-Gln-Gly-Leu-Pro-Gln SEQ ID NO: 1) obtained in Example 2 of the present invention.

TABLE 11

| | |
|---|---|
| Mixed isomerized sugar | 15.4 wt % |
| Fruit juice | 10.0 wt % |
| Citric acid | 0.5 wt % |
| Antioxidative peptide (His-Pro-Ile-Lys-His-Gln-Gly-Leu-pro-Gln SEQ ID NO: 1) | 0.1 wt % |
| Essence | 0.2 wt % |
| Water | 73.8 wt % |

EXAMPLE 13

Production of Cheese Jelly 200 ml of milk and 2.5 g of an agar powder were sufficiently mixed and heated. After, dissolving the agar, 50 g of sugar was added to the mixture and melted. The mixture was then lightly boiled. 150 g of Gouda cheese was torn into bite-sized pieces and added to the mixture in order to incorporate an active ingredient contained in cheese. After removing heat, the mixture was poured into a mold and solidified in a refrigerator to obtain blood adiponectin level increase acceleration and/or decrease inhibition cheese jelly.

EXAMPLE 14

Production of Cheese Powder 10 kg of Gouda cheese was cut using a meat chopper. In order to incorporate an active ingredient contained in the cheese, the cheese was put into a melting tank containing 5 kg of hot water (90° C.) together with molten salt (sodium phosphate: 1.2%, sodium polyphosphate: 1%) and an emulsifier (sugar ester: 0.6%). After adjusting the pH of the mixture to 6.2, the mixture was stirred. Vapor was then blown into the mixture to obtain an emulsion. The emulsion was homogenized, filtered, and spray-dried to obtain a blood adiponectin level increase acceleration and/or decrease inhibition cheese powder.

EXAMPLE 15

Production of Stick Health Food 100 g of the blood adiponectin level increase acceleration and/or decrease inhibition cheese powder obtained in Example 15, 40 g of vitamin C, 100 g of granulated sugar, and 60 g of a mixture of cornstarch and lactose (equal quantity) were mixed. A stick bag was charged with the mixture to obtain a blood adiponectin level increase acceleration and/or decrease inhibition stick health food (100 bags).

The invention claimed is:

1. A method of promoting fat burning in a subject in need thereof, comprising administering to the subject an effective amount of an isolated peptide consisting of the amino acid sequence His-Pro-Ile-Lys-His-Gln-Gly-Leu-Pro-Gln (SEQ ID NO: 1).

2. A method of increasing the level, or suppressing a decrease in the level, of adiponectin in the blood of a subject in need thereof, comprising administering to the subject an effective amount of an isolated peptide consisting of the amino acid sequence His-Pro-Ile-Lys-His-Gln-Gly-Leu-Pro-Gln (SEQ ID NO: 1).

3. A method of promoting fat burning in a subject in need thereof, comprising administering to the subject an effective amount of an isolated peptide consisting of the amino acid sequence His-Pro-Ile-Lys (SEQ ID NO: 2).

4. A method of increasing the level, or suppressing a decrease in the level, of adiponectin in the blood of a subject in need thereof, comprising administering to the subject an effective amount of an isolated peptide consisting of the amino acid sequence His-Pro-Ile-Lys (SEQ ID NO: 2).

5. A method of promoting fat burning in a subject in need thereof, comprising administering to the subject an effective amount of an isolated peptide consisting of the amino acid sequence His-Gln-Gly-Leu-Pro-Gln (SEQ ID NO: 3).

6. A method of increasing the level, or suppressing a decrease in the level, of adiponectin in the blood of a subject in need thereof, comprising administering to the subject an effective amount of an isolated peptide consisting of the amino acid sequence His-Gln-Gly-Leu-Pro-Gln (SEQ ID NO: 3).

* * * * *

SEQUENCE LISTING

```
<160> NUMBER OF SEQ ID NOS: 3

<210> SEQ ID NO 1
<211> LENGTH: 10
<212> TYPE: PRT
<213> ORGANISM: Bovine

<400> SEQUENCE: 1

His Pro Ile Lys His Gln Gly Leu Pro Gln
1               5                   10

<210> SEQ ID NO 2
<211> LENGTH: 4
<212> TYPE: PRT
<213> ORGANISM: Bovine

<400> SEQUENCE: 2

His Pro Ile Lys
1

<210> SEQ ID NO 3
<211> LENGTH: 6
<212> TYPE: PRT
<213> ORGANISM: Bovine

<400> SEQUENCE: 3

His Gln Gly Leu Pro Gln
1               5
```